(12) United States Patent
Penninger et al.

(10) Patent No.: US 11,066,345 B2
(45) Date of Patent: Jul. 20, 2021

(54) PROCESSES FOR INCREASING AN OCTANE VALUE OF A GASOLINE COMPONENT

(71) Applicant: UOP LLC, Des Plaines, IL (US)

(72) Inventors: Michael W. Penninger, Chicago, IL (US); Mark P. Lapinski, Aurora, IL (US); Gregory R. Werba, Arlington Heights, IL (US); David S. Lafyatis, Schaumburg, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/454,526

(22) Filed: Jun. 27, 2019

(65) Prior Publication Data

US 2020/0407655 A1   Dec. 31, 2020

(51) Int. Cl.
| | |
|---|---|
| *C07C 5/333* | (2006.01) |
| *C10L 1/06* | (2006.01) |
| *C07C 5/22* | (2006.01) |
| *C07C 5/367* | (2006.01) |
| *C10L 10/10* | (2006.01) |
| *C10G 61/02* | (2006.01) |

(52) U.S. Cl.
CPC ............ *C07C 5/333* (2013.01); *C07C 5/2206* (2013.01); *C07C 5/367* (2013.01); *C10G 61/02* (2013.01); *C10L 1/06* (2013.01); *C10L 10/10* (2013.01); *C10G 2300/1081* (2013.01); *C10G 2300/80* (2013.01); *C10G 2400/02* (2013.01); *C10G 2400/22* (2013.01); *C10L 2200/0423* (2013.01); *C10L 2270/023* (2013.01)

(58) Field of Classification Search
None
See application file for complete search history.

(56) References Cited

U.S. PATENT DOCUMENTS

| | | | |
|---|---|---|---|
| 7,612,246 B2 | 11/2009 | Broutin et al. | |
| 8,470,165 B2 | 6/2013 | Cosyns et al. | |
| 9,024,097 B2 | 5/2015 | Serban et al. | |
| 9,029,618 B2 | 5/2015 | Serban et al. | |
| 9,079,817 B2 | 7/2015 | Moser et al. | |
| 2005/0258076 A1* | 11/2005 | Houzvicka ........... C10G 35/085 |
| | | | 208/134 |

(Continued)

FOREIGN PATENT DOCUMENTS

GB     1186095     4/1970

*Primary Examiner* — Philip Y Louie
*Assistant Examiner* — Alyssa L Cepluch (57) ABSTRACT

Processes for increasing an octane value of a gasoline component by dehydrogenating a stream comprising $C_7$ hydrocarbons and methylcyclohexane in a first dehydrogenation zone to form an intermediate dehydrogenation effluent, and then dehydrogenating the intermediate dehydrogenation effluent in a second dehydrogenation zone to form a $C_7$ dehydrogenation effluent. The $C_7$ dehydrogenation effluent has an increased olefins content compared to an olefins content of the intermediate dehydrogenation effluent. The first dehydrogenation zone is operated under conditions to convert methylcyclohexane to toluene and minimize cracking reactions. The intermediate dehydrogenation effluent may be heated before being passed to the second dehydrogenation zone.

20 Claims, 1 Drawing Sheet

(56) References Cited

U.S. PATENT DOCUMENTS

| | | | |
|---|---|---|---|
| 2006/0106266 A1* | 5/2006 | Broutin | C10L 1/06 585/418 |
| 2009/0301934 A1* | 12/2009 | Miller | C10G 35/09 208/65 |
| 2013/0158320 A1 | 6/2013 | Moser et al. | |
| 2014/0378700 A1 | 12/2014 | Majumder et al. | |

\* cited by examiner

PROCESSES FOR INCREASING AN OCTANE VALUE OF A GASOLINE COMPONENT

FIELD OF THE INVENTION

This invention relates generally to a process for producing high octane gasoline and more particularly to processes which incorporate a dehydrogenation unit increase the octane value of a gasoline component by converting $C_7$ saturated hydrocarbons to their corresponding olefins.

BACKGROUND OF THE INVENTION

Gasoline specifications are becoming stricter and more difficult for refiners to meet. For hydrocracker-based refineries, which rely on the reforming and isomerization units to produce gasoline, it is difficult to meet the aromatics specifications in the Euro V gasoline standard while maximizing 95 RON (research octane number). Euro V standards limit gasoline to concentrations of no more than 35 lv % aromatics and no more than 1.0 lv % benzene with additional limitations on distillation and Reid vapor pressure (RVP). It is common that a refiner cannot process as much reformer feed due to the aromatics limitation thus resulting in the need to sell heavy naphtha that has lower value, thus reducing the refiner's profitability. A refiner can add oxygenates such as methyl tert-butyl ether (MTBE) or tertiary amyl methyl ether (TAME) to the gasolines to increase octane, but these can be expensive and there may be additional environmental regulations against these compounds. The Euro V specifications also limit the amount of olefins that can be added to the gasolines to 18 lv %. For hydrocracker-based, condensate-based or other refineries that do not add a significant amount of olefins to the gasolines, producing an olefin stream can be advantageous due to an increase in octane over paraffins. Since these refineries have low olefins in their gasolines, a significant amount of olefins can be blended into the gasolines up to the specification.

In a typical naphtha complex configuration, a naphtha splitter distillation column fractionates a hydrotreated full range naphtha stream into light naphtha and heavy naphtha. The light naphtha stream containing $C_5$ and $C_6$ species goes to the isomerization unit to make an isomerate and the $C_7+$ heavy naphtha is processed in the reforming unit to make reformate. It would be desirable to separate the $C_7$ components from the heavy stream and upgrade the octane of these components via isomerization to higher octane isoparaffins and via dehydrogenation to higher octane olefins instead of converting the $C_7$ components to aromatics in the reformer, thus allowing more of the naphtha to be blended to the gasoline pool. Since the fractionated $C_7$ stream can contain appreciable methylcyclohexane (MCH), processing in a dehydrogenation unit will produce toluene and a significant endotherm that will quench the dehydrogenation reactions of the remaining $C_7$ components. Therefore, it would be desirable to provide processes which take advantage of the benefits of dehydrogenating the $C_7$ paraffins which include appreciable amounts of MCH in the feed to a $C_7$ dehydrogenation unit.

SUMMARY OF THE INVENTION

The present invention provides processes allow for a refiner to appreciate the benefits of dehydrogenating the $C_7$ hydrocarbons in dehydrogenation unit feeds which include appreciable amounts of MCH. A $C_7$ stream is first fractionated from the naphtha splitter and processed in an isomerization zone forming an effluent with increased isoparaffins, and then processed in a dehydrogenation zone that converts MCH into toluene and partially converts paraffins, isoparaffins, and cyclopentane compounds to higher octane mono-olefins. Due to the endothermic nature of dehydrogenation and the potential amounts of MCH (0.1-40%) in $C_7$ fractionated cuts, in order to realize the octane boost delivered from the generation of $C_7$ olefinic species, the processes utilize a multi-reactor dehydrogenation system in which MCH is run as nearly as possible to the equilibrium conversion within the first dehydrogenation reactor. The first dehydrogenation reactor effluent is then reheated with the use of inter-stage heating to bring the stream up to temperature to partially dehydrogenate $nC_7$, $iC_7$, and $C_7$ cycloparaffins in the second dehydrogenation reactor to produce normal, multi-branched and cyclic olefins. The processing benefit to this approach allows one to lower the net amount of $C_7$ components that are converted into aromatics while gaining a large octane boost from the branched and cyclic $C_7$ olefins for blending to a gasoline pool.

Even though the processes of the present invention produce toluene, the net amount of $C_7$ components that are converted into aromatics are significantly less compared to sending all the $C_7$ components to a reforming unit. In a reforming unit, for example, $C_7$ paraffins and isoparaffins react to form rings that dehydrogenate to aromatics, $C_7$ cyclopentanes isomerize to MCH and then dehydrogenate to toluene, and MCH is directly dehydrogenated to toluene. In the current processes, a significant portion of the $C_7$ paraffins, $C_7$ isoparaffins, and $C_7$ cyclopentane compounds are not converted to aromatics.

Therefore, the present invention may be characterized, in at least one aspect, as providing a process for increasing an octane value of a gasoline component by: separating a naphtha feed in a naphtha splitter into a stream comprising $C_6$ and lighter boiling hydrocarbons, a $C_7$ stream comprising $C_7$ hydrocarbons including methylcyclohexane, and a heavy stream comprising $C_8$ hydrocarbons; dehydrogenating at least a portion of the stream comprising $C_7$ hydrocarbons in a first dehydrogenation zone to form an intermediate dehydrogenation effluent, the first dehydrogenation zone comprising a catalyst and operated under conditions to convert methylcyclohexane to toluene and minimize cracking reactions; dehydrogenating the intermediate dehydrogenation effluent in a second dehydrogenation zone to form a $C_7$ dehydrogenation effluent, the $C_7$ dehydrogenation zone comprising a catalyst and the $C_7$ dehydrogenation effluent comprising an increased olefins content compared to an olefins content of the intermediate dehydrogenation effluent; and, blending the $C_7$ dehydrogenation effluent as a gasoline component in a gasoline pool. The process may include heating the intermediate dehydrogenation effluent before dehydrogenating the intermediate dehydrogenation effluent in the second dehydrogenation zone. The first dehydrogenation zone may have a lower inlet temperature than the second dehydrogenation zone. The first dehydrogenation zone may be operated with an inlet temperature of between about 400 to 450° C. and the second dehydrogenation zone may be operated with an inlet temperature of about 550° C. The second dehydrogenation zone may be operated to convert between 15-25% to olefins. The $C_7$ dehydrogenation effluent may include mono-olefins. The process may further include isomerizing the stream comprising $C_7$ hydrocarbons, in an isomerization zone comprising a catalyst and operated under conditions to isomerize the $C_7$ hydrocarbons, to provide a $C_7$ isomerized effluent. The $C_7$ isomerized effluent may be the at least a portion of the stream comprising $C_7$ hydrocarbons dehydrogenated in the first dehydrogenation zone. The catalyst in the first dehydrogenation zone and the catalyst in the second dehydrogenation zone may be the same. The process may also include isomerizing at least a portion of the stream comprising $C_6$ and lighter boiling hydrocarbons, in a $C_6$ isomerization zone at isomerization conditions, to form a $C_6$ isomerization effluent, reforming the heavy stream, in a reforming zone under reforming conditions, to form a reformate stream, and, blending the $C_6$ isomerization effluent and the reformate stream with the $C_7$ dehydrogenation effluent in the gasoline pool. The process may still further include sensing at least one parameter of the process and generating a signal or data from the sensing, generating and transmitting a signal; or generating and transmitting data.

In a second aspect, the present invention may generally be characterized as providing a process for increasing an octane value of a gasoline component by: separating a naphtha feed in a naphtha splitter into a stream comprising $C_6$ and lighter boiling hydrocarbons, a $C_7$ stream comprising $C_7$ hydrocarbons including methylcyclohexane, and a heavy stream comprising $C_8$ hydrocarbons; isomerizing the stream comprising $C_7$ hydrocarbons in an isomerization zone to provide a $C_7$ isomerized effluent, the isomerization zone comprising a catalyst and operated under conditions to isomerize the $C_7$ hydrocarbons; dehydrogenating the $C_7$ isomerized effluent in a first dehydrogenation zone to form an intermediate dehydrogenation effluent, the first dehydrogenation zone comprising a catalyst and operated under conditions to convert methylcyclohexane to toluene and minimize cracking reactions; dehydrogenating the intermediate dehydrogenation effluent in a second dehydrogenation zone to form a $C_7$ dehydrogenation effluent, the second dehydrogenation zone comprising a catalyst and the $C_7$ dehydrogenation effluent comprising an increased olefins content compared to an olefins content of the intermediate dehydrogenation effluent; and, blending the $C_7$ dehydrogenation effluent as a gasoline component in a gasoline pool. The process may include heating the intermediate dehydrogenation effluent before dehydrogenating the intermediate dehydrogenation effluent in the second dehydrogenation zone. The first dehydrogenation zone may have a lower inlet temperature than the second dehydrogenation zone. The first dehydrogenation zone may be operated with an inlet temperature of between about 400 to 450° C. (752 to 842° F.) and the second dehydrogenation zone may be operated with an inlet temperature of about 550° C. (1022° F.). The second dehydrogenation zone may be operated to covert between 15-25% olefins. The $C_7$ dehydrogenation effluent comprises mono-olefins. The catalyst in the first dehydrogenation zone and the catalyst in the second dehydrogenation zone may be the same. The process may further include sensing at least one parameter of the process and generating a signal or data from the sensing, generating and transmitting a signal, or generating and transmitting data.

In a third aspect, the present invention broadly may be characterized as providing a process for increasing an octane value of a gasoline component by: separating a naphtha feed in a naphtha splitter into a stream comprising $C_6$ and lighter boiling hydrocarbons, a $C_7$ stream comprising $C_7$ hydrocarbons including methylcyclohexane, and a heavy stream comprising $C_8$ hydrocarbons; isomerizing at least a portion of the stream comprising $C_6$ and lighter boiling hydrocarbons, in a $C_6$ isomerization zone at isomerization conditions, to form a $C_6$ isomerization effluent; isomerizing the stream comprising $C_7$ hydrocarbons, in an isomerization zone comprising a catalyst and operated under conditions to isomerize the $C_7$ hydrocarbons, to form a $C_7$ isomerized effluent; dehydrogenating the $C_7$ isomerized effluent in a first dehydrogenation zone to form an intermediate dehydrogenation effluent, the first dehydrogenation zone comprising a catalyst and operated under conditions to convert methylcyclohexane to toluene and minimize cracking reactions; heating the intermediate dehydrogenation effluent and then dehydrogenating the intermediate dehydrogenation effluent in a second dehydrogenation zone to form a $C_7$ dehydrogenation effluent, the second dehydrogenation zone comprising a catalyst, the $C_7$ dehydrogenation effluent comprising an increased olefins content compared to an olefins content of the intermediate dehydrogenation effluent; reforming the heavy stream, in a reforming zone under reforming conditions, to form a reformate stream; and, blending the $C_6$ isomerization effluent, the $C_7$ dehydrogenation effluent as the gasoline component, and the reformate stream in a gasoline pool. The first dehydrogenation zone may be operated with an inlet temperature of between about 400 to 450° C. (752 to 842° F.) and the second dehydrogenation zone may be operated with an inlet temperature of about 550° C. (1022° F.).

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which the FIGURE depicts an exemplary process flow diagram according to one or more embodiments of the present invention.

DETAILED DESCRIPTION OF THE INVENTION

Figure 1:
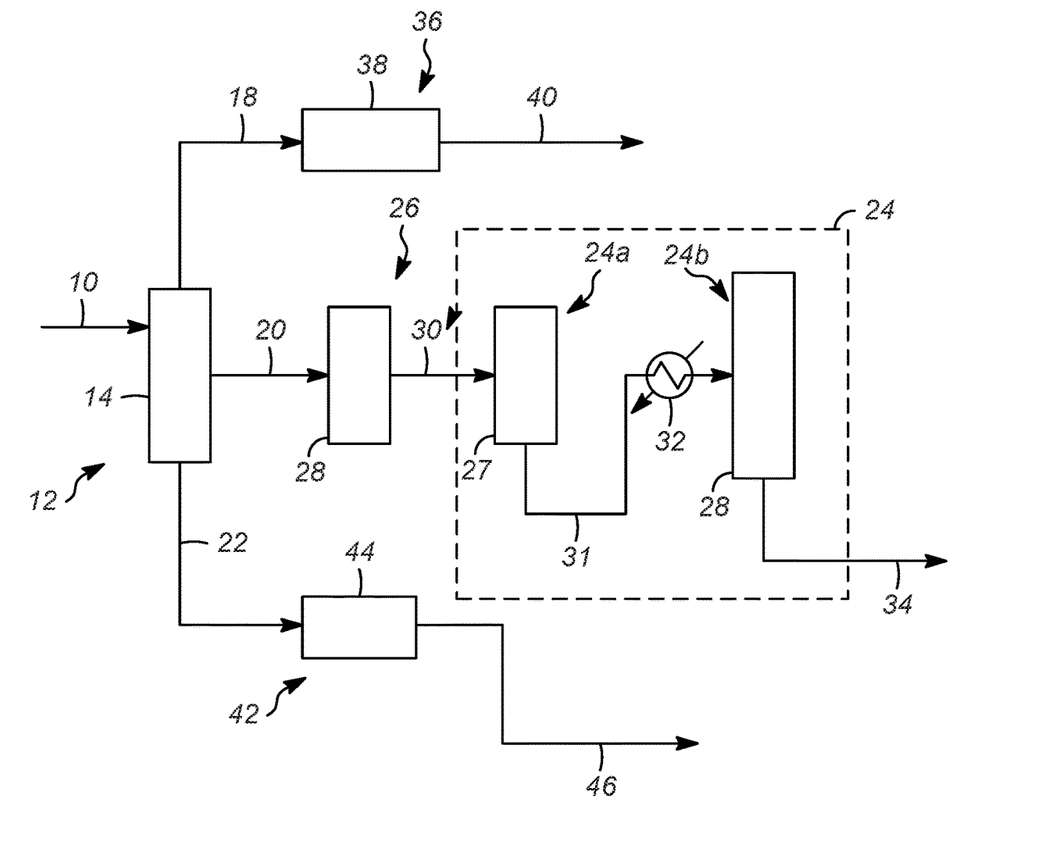

As mentioned above, processes have been invented for the effective and efficient dehydrogenation of a $C_7$ naphtha cut which includes MCH. Generally, a $C_7$ cut from a naphtha splitter is first isomerized in an isomerization zone to convert some normal and single-branched paraffins to multi-branched $C_7$ paraffins. $C_7$ cyclopentanes and MCH can also be isomerized. The production of the multi-branched $C_7$ isoparaffins allows conversion to $C_7$ multi-branched mono-olefins in the subsequent dehydrogenation zone which have higher octane numbers than mono-olefins formed from $C_7$ normal paraffins. The liquid effluent from the isomerization zone passes to a heater and then to the first dehydrogenation zone which includes a reactor operating at, for example, 400 to 450° C. (752 to 842° F.) to minimize cracking of the $C_7$ components while reacting the MCH to toluene to equilibrium (about 100% conversion). Temperature drops of 50 to 100° C. are possible in the reactor of the first dehydrogenation stage. An intermediate dehydrogenation effluent would then be heated to a higher inlet temperature for the reactor in the second dehydrogenation stage, for example to 550° C. (1022° F.). In the second stage reactor, n-paraffins, iso-paraffins and cyclopentanes will dehydrogenate to olefins. Preferably, the reactors are operated with a 15-25% single pass conversion of $C_7$ species to olefins to minimize cracking reactions at these temperatures. The dehydrogenation effluent from the second reactor may then be blended with other components in a gasoline pool to bolster octanes. Additional stages of reheat and dehydrogenation may be added to increase the olefin conversion, but the cost of reheat, extra reactors and losses of gasoline product to light ends may be uneconomical. Additionally, the dehydrogenation effluent can be sent to a selective hydrogenation zone to convert any di-olefins to mono-olefins since di-olefins are undesired in gasoline pools due to the higher potential for gum formation.

With these general principles in mind, one or more embodiments of the present invention will be described with the understanding that the following description is not intended to be limiting.

As shown in the FIGURE, a naphtha feed stream 10 comprising C5-C12 is sent to a fractionation zone 12 having a fractionation column 14, such as a naphtha splitter. In the fractionation column 14, the naphtha feed stream 10 is separated into a C5/C6 rich stream 18, a C7 stream 20, and a heavy stream 22. The naphtha feed stream 10 may have a wider range of hydrocarbons, and may be first treated in, for example, a hydrotreating unit (not shown) before being separated in the fractionation column. The C5/C6 rich stream 18 comprises C6 and lighter boiling hydrocarbons, the C7 stream 20 comprises C7 hydrocarbons including MCH and the heavy stream 22 comprises C8 and heavier hydrocarbons.

The $C_7$ stream 20 is passed first to a $C_7$ isomerization zone 26. The $C_7$ isomerization zone 26 comprises at least one reactor 28 with an isomerization catalyst and is operated under conditions for converting normal and single branched paraffins in the $C_7$ stream into multi-branched paraffins. Additionally, within the $C_7$ isomerization zone 26 some $C_7$ cyclopentanes and some MCH may also be isomerized.

Any suitable isomerization catalyst may be used in the $C_7$ isomerization zone 26. Suitable isomerization catalysts include acidic catalysts using chloride for maintaining the sought acidity and sulfated catalysts. The isomerization catalyst may be amorphous, e.g., based upon amorphous alumina, or zeolitic. A zeolitic catalyst would still normally contain an amorphous binder. The catalyst may include a sulfated zirconia and platinum as described in U.S. Pat. No. 5,036,035 and European application 0 666 109 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst including a tungstated support of an oxide or hydroxide of a Group IVB (TUPAC 4) metal, for example zirconium oxide or hydroxide, at least a first component which is a lanthanide element and/or yttrium component, and at least a second component being a platinum-group metal component.

Contacting within the reactor 28 of the isomerization zone 26 may be effected using the catalyst in a fixed-bed system, a moving-bed system, a fluidized-bed system, or in a batch-type operation. A fixed-bed multi-reactor system may be employed in an exemplary embodiment. The reactants may be contacted with the bed of catalyst particles in upward, downward, or radial-flow fashion. The reactants may be in the liquid phase, a mixed liquid-vapor phase, or a vapor phase when contacted with the catalyst particles. The isomerization zone 26 can also include feed-effluent heat exchangers, inter-reactor heat exchangers, driers, sulfur guards, separator, stabilizer, compressors, separation columns, recycle streams and other equipment as known in the art (not shown). A hydrogen-rich gas stream (not shown) is typically mixed with stream 20 and heated to reaction temperatures. The hydrogen-rich gas stream, for example, comprises about 50-100 mol % hydrogen. The hydrogen can be separated from the reactor effluent, compressed and recycled back to mix with the light stream. Stream 20 and hydrogen are contacted in the $C_7$ isomerization zone 26 with an isomerization catalyst forming a $C_7$ isomerization effluent 30.

Isomerization conditions in reactor 28 of the isomerization zone 26 may include reactor temperatures that may be from 40 to 250° C. (104 to 482° F.). Lower reaction temperatures (within the stated range) may be employed to favor equilibrium mixtures having the highest concentration of high-octane highly branched isoalkanes and to minimize cracking of the feed to lighter hydrocarbons. Temperatures from 100 to 200° C. (212 to 392° F.) may be employed in some embodiments. Reactor operating pressures may be from 100 kPa to 10 MPa absolute (14.5 to 1,450 psi), for example from 0.5 MPa to 4 MPa absolute (72.5 to 580 psi). Liquid hourly space velocities may be from 0.2 to 25 volumes of isomerizable hydrocarbon feed per hour per volume of catalyst, for example from 0.5 to 15 hr'.

A $C_7$ isomerized effluent 30 is combined with a hydrogen stream (not shown), heated and passed to the dehydrogenation zone 24. The dehydrogenation zone 24 according to the present invention comprises a first dehydrogenation zone 24a and a second dehydrogenation zone 24b. Each dehydrogenation zone 24a, 24b includes a reactor 27, 28 which contains a catalyst to convert a portion of the saturated hydrocarbons in the $C_7$ isomerized effluent 30 to olefins in the presence of hydrogen over a selective dehydrogenation catalyst. Specifically, normal paraffins are dehydrogenated to the corresponding normal mono-olefins. For example, normal-heptane is dehydrogenated to the mono-olefins 1-heptene, trans-2-heptene, trans-3-heptene, cis-2-heptene, and cis-3-heptene. Isoparaffins are dehydrogenated to the corresponding mono-iso-olefins. For example, 2,4-dimethylpentane is dehydrogenated to 2,4-dimethyl-1-pentene and 2,4-dimethyl-2-pentene. Cyclopentane compounds are dehydrogenated to cyclopentene compounds. Cyclohexane compounds are dehydrogenated to aromatic compounds. Additionally, as indicated above, within the dehydrogenation zone 24, MCH is converted to toluene.

The dehydrogenation process may utilize any suitable selective dehydrogenation catalyst. Generally, one preferred suitable catalyst comprises a Group VIII noble metal component (e.g., platinum, iridium, rhodium, and palladium), an alkali metal component, and a porous inorganic carrier material. The catalyst may also contain promoter metals which advantageously improve the performance of the catalyst. The porous carrier material should be relatively refractory to the conditions utilized in the reaction zone and may be chosen from those carrier materials which have traditionally been utilized in dual function hydrocarbon conversion catalysts. A preferred porous carrier material is a refractory inorganic oxide, with the most preferred an alumina carrier material. The particles are usually spheroidal and have a diameter of from about 1.6 to about 3.2 mm (about 1/16 to about 1/8 inch), although they may be as large as about 6.4 mm (about 1/4 inch). Newer dehydrogenation catalysts can also be used in this process.

For example, one such catalyst comprises a layered catalyst composition comprising an inner core, and outer layer bonded to the inner core so that the attrition loss is less than 10 wt % based on the weight of the outer layer. The outer layer is a refractory inorganic oxide. Uniformly dispersed on the outer layer is at least one platinum group metal, and a promoter metal. The inner core and the outer layer are made of different materials. A modifier metal is also dispersed on the outer layer. The inner core is made from alpha alumina, theta alumina, silicon carbide, metals, cordierite, zirconia, titania, and mixtures thereof. The outer refractory inorganic oxide is made from gamma alumina, delta alumina, eta alumina, theta alumina, silica/alumina, zeolites, non-zeolitic molecular sieves, titania, zirconia, and mixtures thereof. The platinum group metals include platinum, palladium, rhodium, iridium, ruthenium, osmium, and mixtures thereof. The platinum group metal is present in an amount from about 0.01 to about 5 wt % of the catalyst composition. The promoter metal includes tin, germanium, rhenium, gallium, bismuth, lead, indium, cerium, zinc, and mixtures thereof. The modifier metal includes alkali metals, such as potassium and lithium, alkaline earth metals, and mixtures thereof. Further discussion of two layered dehydrogenation catalysts can be found in U.S. Pat. No. 6,617,381, which is incorporated herein by reference, for example.

The process conditions utilized for dehydrogenation are usually 0 to 345 kPa (0 to 50 psig), 0.5 to 6 hydrogen/hydrocarbon mole ratio, inlet reactor temperatures of 450 to 600° C. (845 to 1112° F.), and 1 to 30 $h^{-1}$ LHSV. Conditions preferred for $C_7$ hydrocarbon feed stocks are about 138 to 276 kPa (20 to 40 psig), about 3 to 5 hydrogen/hydrocarbon mole ratio, inlet reactor temperatures of about 520 to 565° C. (968 to 1049° F.), and about 5 to 10 $h^{-1}$ LHSV. An important feature of the present invention is that the conditions in the two reactors 27, 28 are different so as convert MCH to toluene in the first reactor 27 while minimizing cracking reactions and then maximizing the dehydrogenation of the paraffins in the second reactor 28 while minimizing cracking. Adiabatic radial-flow reactors are used to minimize pressure drop within an efficient reactor volume. Hydrogen and some by-product light ends are typically separated (not shown) from the dehydrogenation reactor effluent 34, and a part of this hydrogen gas may be recycled back to the dehydrogenation reactors 27, 28 to minimize coking and enhance catalyst stability.

Accordingly, the reactor 27 of the first dehydrogenation zone 24a is preferably operated with a temperature of between about 400 to 450° C. (752 to 842° F.) to minimize cracking products and take advantage of MCH equilibrium conversion to toluene which is about 100% conversion. An intermediate dehydrogenation effluent 31 from the reactor 27 of the first dehydrogenation zone 24a is heated in a heater 32, such as a heat exchanger or a fired heater, to 550° C. (1022° F.) and passed to the reactor 28 of the second dehydrogenation zone 24b. The reactor 28 in the second dehydrogenation zone 24b is preferably operated with an inlet temperature of about 550° C. (1022° F.) to dehydrogenate n-paraffins, iso-paraffins and cyclopentanes to olefins. As noted above, the dehydrogenation zone 24 is preferably operated with conditions suitable for a 15-25% single pass conversion of $C_7$ species to minimize the cracking at these temperatures.

An $C_7$ dehydrogenation effluent 34 comprising an increased olefins content compared to an olefins content of the intermediate dehydrogenation effluent 31 may be added to a gasoline pool to bolster octane value of the gasoline blend. Although not depicted as such, it is contemplated that the $C_7$ dehydrogenation effluent 34 is passed to a selective hydrogenation zone (not shown in the FIGURE) for the selective conversion of small amounts of diolefins to mono-olefins before being blended in the gasoline pool. In such a process, a hydrogen stream is also charged to the selective hydrogenation reactor. Typical selective hydrogenation conditions utilized are about 25 to 350° C. (77 to 662° F.), about 276 kPa to 5.5 MPa (40 to 800 psig), 5-35 $h^{-1}$ LHSV and a hydrogen to diolefin mole ratio of between about 1.4 to 2.0. The selective hydrogenation reactor effluent passes to a stripper where dissolved light hydrocarbons are removed and the stripper bottoms, a mixture of mono-olefin hydrocarbons and unconverted saturated hydrocarbons, is sent for blending in gasoline pool.

Returning to the fractionation zone 12, in the present processes the $C_5/C_6$ rich stream 18 may be passed to a $C_5/C_6$ isomerization zone 36, which includes a reactor 38 comprising a suitable isomerization catalyst and which is operated under conditions to convert the normal hydrocarbons in the $C_5/C_6$ rich stream 18 into branched hydrocarbons. The $C_5/C_6$ isomerization zone 36 can be any type of isomerization zone that takes a stream of $C_5/C_6$ straight-chain hydrocarbons or a mixture of straight-chain, branched-chain, cyclic hydrocarbons, and benzene and converts straight-chain hydrocarbons in the feed mixture to branched-chain hydrocarbons and branched hydrocarbons to more highly branched hydrocarbons, thereby producing an effluent having branched-chain and straight-chain hydrocarbons. The cycloparaffins can isomerize between cyclopentanes and cyclohexane compounds. Benzene can be saturated to form cyclohexane. In some embodiments, the $C_5/C_6$ isomerization zone 36 can include one or more isomerization reactors, feed-effluent heat exchangers, inter-reactor heat exchangers, driers, sulfur guards, separator, stabilizer, compressors, deisopentanizer column, deisohexanizer column, recycle streams and other equipment as known in the art (not shown). An isomerization effluent 40 from the $C_5/C_6$ isomerization zone 36 may be blended in the gasoline pool as well.

Additionally, the heavy stream 22 from the fractionation zone 12 may be passed to a reforming zone 42. Generally, the reforming zone 42 includes a number of reactors (or reaction zones) 44, but usually the number of reactors is three, four, or five. Since reforming reactions occur generally at an elevated temperature and are generally endothermic, each reactor 44 usually has one or more heating zones associated with it, which heat the reactants to the desired reaction temperature.

Typical feed inlet temperature for the reforming zone 42 are between 440 to 580° C. (824 and 1076° F.), or between 500 and 580° C. (932 and 1076° F.), or between 540 and 580° C. (1004 and 1076° F.), or at least above 540° C. (932° F.). The reformer reactors 44 may have different operating temperatures, for example, a first reforming reactor having a temperature between 500 to 540° C. (932 to 1004° F.) and a second, subsequent reforming reactor having a temperature greater than 540° C. (1004° F.). The reforming zone 42 can be operated at a range of pressures generally from atmospheric pressure of about 0 to about 6,895 kPa(g) (about 0 psig to about 1,000 psig), or about 276 to about 1,379 kPa(g) (about 40 to about 200 psig). The reaction conditions also include a liquid hour space velocity (LHSV) in the range from 0.6 $h^{-1}$ to 10 $h^{-1}$. Preferably, the LHSV is between 0.6 $h^{-1}$ and 5 $h^{-1}$, with a more preferred value between 1 $h^{-1}$ and 5 $h^{-1}$, and with a most preferred value between 2 $h^{-1}$ and 5 $h^{-1}$. The shorter residence time is especially preferred when utilizing the higher temperatures. The catalyst also has a residence time in the reformers of between 0.5 hours and 36 hours.

Due to coke build-up on reforming catalysts during normal operations, the catalyst must be periodically regenerated to re-establish fresh performance. The reforming zone 42 in the present invention can be of any type including cyclic, semi-regenerative or continuous regeneration. For a continuously regenerated reformer, the process can employ catalyst particles in several reaction zones interconnected in a series flow arrangement. The catalyst particles in the reformer are typically comprised of one or more Group VIII (IUPAC 8-10) noble metals (e.g., platinum, iridium, rhodium, and palladium) and a halogen combined with a porous carrier, such as a refractory inorganic oxide. U.S. Pat. No. 2,479,110, for example, teaches an alumina-platinum-halogen reforming catalyst. Although the catalyst may contain about 0.05 to about 2.0 wt-% of Group VIII metal, a less expensive catalyst, such as a catalyst containing about 0.05 to about 0.5 wt-% of Group VIII metal may be used. In addition, the catalyst may contain indium and/or a lanthanide series metal such as cerium. The catalyst particles may also contain one or more Group IVA (IUPAC 14) metals (e.g., tin, germanium, and lead), such as described in U.S. Pat. Nos. 4,929,333, 5,128,300, and the references cited therein. The halogen is typically chlorine, and alumina is commonly the carrier. Suitable alumina materials include, but are not limited to, gamma, eta, and theta alumina. One property related to the performance of the catalyst is the surface area of the carrier. Preferably, the carrier has a surface area of about 100 to about 500 m$^2$/g. The activity of catalysts having a surface area of less than about 130 m$^2$/g tend to be more detrimentally affected by catalyst coke than catalysts having a higher surface area. Generally, the particles are usually spheroidal and have a diameter of about 1.6 to about 3.1 mm (about 1/16 to about 1/8 inch), although they may be as large as about 6.35 mm (about 1/4 inch) or as small as about 1.06 mm (about 1/24 inch). In a particular reforming reaction zone, however, it is desirable to use catalyst particles which fall in a relatively narrow size range.

An effluent stream 46 from the reforming zone 42 may also be blended with the C$_7$ dehydrogenation effluent 34 and the isomerization effluent 40 for the gasoline blend.

Example 1

When nC$_7$ is dehydrogenated to the corresponding normal C$_7$ mono-olefins, the octane numbers range between 54.5 to 90.2 RON with an average of 77.0 RON as listed in Table 1, below. When a single-branched iC$_7$ paraffin such as 3-methylhexane is dehydrogenated to the corresponding iC$_7$ mono-olefins, the octane numbers range between 82.2 to 98.6 RON with an average of 92.5 RON. When multi-branched iC$_7$ paraffins such as 2,2-dimethylpentane, 2,4-deimethylpentane and 3,3-deimethylpentane are dehydrogenated to the corresponding multi-branched iC$_7$ mono-olefins, the octane numbers range from 99.2 to 105.3 RON with averages of 100.2-103.1 RON as shown in Table 1. Therefore, in terms of octane increase, it is more advantageous to dehydrogenate single-branched iC$_7$ paraffins as compared to nC$_7$ and it is most advantageous to dehydrogenate multi-branched iC$_7$ paraffins which have the highest mono-olefin octanes.

TABLE 1

Pure component octanes (RON) for C$_7$ paraffins and mono-olefins.

| Paraffin | Corresponding Mono-Olefins | API Database RON | Phillip 66 Database RON |
|---|---|---|---|
| nC$_7$ | 1-heptene | 54.5 | 54.5 |
|  | t-2-heptene | 73.4 | 73.4 |
|  | t-3-heptene | 89.8 | 89.8 |
|  | c-3-heptene | 90.2 | 90.2 |
|  | Average | 77.0 | 77.0 |
| 3-MH | 3-methyl-1-hexene | 82.2 | 82.2 |
|  | 4-methyl-1-hexene | 86.4 | 86.4 |
|  | cis-3-methyl-2-hexene | 92.4 | 92.4 |
|  | trans-3-methyl-2-hexene | 91.5 | 91.5 |
|  | cis-4-methyl-2-hexene | 98.6 | 98.6 |

TABLE 1-continued

Pure component octanes (RON) for C$_7$ paraffins and mono-olefins.

| Paraffin | Corresponding Mono-Olefins | API Database RON | Phillip 66 Database RON |
|---|---|---|---|
|  | trans-4-methyl-2-hexene | 96.8 | 96.8 |
|  | cis-3-methyl-3-hexene | 96.0 | 96.0 |
|  | trans-3-methyl-3-hexene | 96.4 | 96.4 |
|  | Average | 92.5 | 92.5 |
| 2,2-DMP | 4,4-dimethyl-1-pentene | 100.4 | 105.4 |
|  | 4,4-dimethyl-c-2-pentene | 100.5 | 105.3 |
|  | 4,4-dimethyl-t-2-pentene | 100.5 | 105.3 |
| 2,4-DMP | 2,4-dimethyl-1-pentene | 99.2 | 99.2 |
|  | 2,4-dimethyl-2-pentene | 100.0 | 100.0 |
| 3,3-DMP | 3,3-dimethyl-1-pentene | 100.3 | 103.5 |
|  | Average | 100.2 | 103.1 |

Example 2

A commercial naphtha composition was obtained and a C$_7$ component cut contained 30.2 wt % n-heptane, 13.0 wt % 2-methylhexane, 15.7 wt % 3-methylhexane, 1.1 wt % 3-ethylpentane, 4.4 wt % multi-branched C$_7$ isoparaffins, 18.6 wt % C$_7$ cyclopentanes, and 17.0 wt % methylcyclohexane. The octane number was estimated to be 55.1 RON. Process simulations were conducted on this stream composition which consisted of a single isomerization reactor simulation operating at about 1.9 MPa (275 psig), 4 h$^{-1}$ LHSV, 110° C. (230° F.) reactor inlet temperature, 0.05 hydrogen/hydrocarbon outlet mole ratio with a chlorided alumina isomerization catalyst.

The isomerized liquid product was predicted to contain 13.1 wt % n-heptane, 16.8 wt % 2-methylhexane, 15.5 wt % 3-methylhexane, 1.2 wt % 3-ethylpentane, 17.1 wt % multi-branched C$_7$ isoparaffins, 9.4 wt % C$_7$ cyclopentanes, and 26.8 wt % methylcyclohexane. Comparing the feed to the isomerized product, the isomerization shifted the n-heptane to both single-branched C$_7$ isoparaffins and multi-branched C$_7$ isoparaffins and some of the C$_7$ cyclopentanes to methylcyclohexane.

From pilot plant data using a selective dehydrogenation catalyst (layered catalyst with the outer layer comprising gamma alumina with dispersed metals Pt, Sn, and Li), a simulation of the dehydrogenation process was developed. The isomerized product was simulated as feed to a single stage dehydrogenation unit (Case A, TABLE 2, below) with 565° C. reactor inlet temperature, 20 psig, 10 h$^{-1}$ LHSV, and hydrogen/hydrocarbon mole ratio of 3. The isomerized product was also simulated in a 2-stage dehydrogenation unit with the first stage (Case B1, TABLE 2, below) operating at 450° C. (842° F.) reactor inlet temperature, about 138 kPa (20 psig), 10 h$^{-1}$ LHSV and hydrogen/hydrocarbon mole ratio of 3 and the second stage (Case B2, TABLE 2, below) operating at 550° C. (1022° F.) reactor inlet temperature, about 138 kPa (20 psig), 10 h$^{-1}$ LHSV and hydrogen/hydrocarbon mole ratio of 3. The effluent from the first stage was fed to the second stage.

The results of the dehydrogenation simulations for a unit with only a single stage (Case A) and a unit with the two stages (Cases B1 and B2) are shown in TABLE 2, below. When the isomerized product with a high concentration of MCH is processed in a single stage dehydrogenation unit, the MCH converts to toluene with a very large temperature drop that prevents significant conversion of C$_7$ paraffins and C$_7$ cyclopentanes to C$_7$ olefins. At high inlet temperatures, there is also about a 3% conversion of C$_7$ paraffins to toluene. This small amount of toluene formed from $C_7$ paraffin is thought to occur on the metal sites at high temperatures via a sequential dehydrogenation pathway.

For the two-stage dehydrogenation unit, the isomerized product was reacted at a lower inlet temperature of 450° C. (842° F.) in the first stage which converts the MCH to toluene with no reaction of the $C_7$ paraffins and $C_7$ cyclopentanes to olefins. The first stage effluent, now without MCH, is fed to the second stage where the $C_7$ paraffins and $C_7$ cyclopentanes react to form olefins with a moderate temperature drop as shown in Table 2 Case B2. The conversion of $C_7$ paraffins to olefins was 19% while the conversion of $C_7$ cyclopentanes to $C_7$ cyclopentenes was about 39%. The octane of the dehydrogenation effluent from the 2-stage unit was higher, 78.1 RON, than the effluent from the single-stage unit, 74.4 RON.

TABLE 2

Simulation results for dehydrogenation of an isomerized $C_7$ stream.

| Dehydrogenation Case | A | B1 | B2 |
|---|---|---|---|
| Dehydro Stages | 1 | 2 | |
| MCH in Dehydro Feed, wt % | 26.8 | 26.8 | 0 |
| Inlet Temperature, ° C. | 565 | 450 | 550 |
| Outlet Temperature, ° C. | 418 | 396 | 512 |
| MCH Conversion, % | 100 | 100 | — |
| $C_7$ Paraffin Conversion to Olefins, % | 0.2 | 0.0 | 19.0 |
| $C_7$ Cyclopentane Conversion to Olefins, % | 0 | 0 | 38.7 |
| $C_{4+}$ RON | 74.4 | 66.7 | 78.1 |
| Multi-branched $C_7$ Olefins, LV % | 0.0 | 0.0 | 3.3 |
| Single-branched $C_7$ Olefins, LV % | 0.1 | 0.0 | 6.4 |
| Normal $C_7$ Olefins, LV % | 0.0 | 0.0 | 2.5 |
| $C_7$ Cyclic Olefins, LV % | 0.0 | 0.0 | 3.6 |
| Toluene, LV % | 24.1 | 21.6 | 24.0 |

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

SPECIFIC EMBODIMENTS

While the following is described in conjunction with specific embodiments, it will be understood that this description is intended to illustrate and not limit the scope of the preceding description and the appended claims.

A first embodiment of the invention is a process for increasing an octane value of a gasoline component, the process comprising separating a naphtha feed in a naphtha splitter into a stream comprising $C_6$ and lighter boiling hydrocarbons, a $C_7$ stream comprising $C_7$ hydrocarbons including methylcyclohexane, and a heavy stream comprising $C_8$ hydrocarbons; dehydrogenating at least a portion of the stream comprising $C_7$ hydrocarbons in a first dehydrogenation zone to form an intermediate dehydrogenation effluent, the first dehydrogenation zone comprising a catalyst and operated under conditions to convert methylcyclohexane to toluene and minimize cracking reactions; dehydrogenating the intermediate dehydrogenation effluent in a second dehydrogenation zone to form a $C_7$ dehydrogenation effluent, the $C_7$ dehydrogenation zone comprising a catalyst and the $C_7$ dehydrogenation effluent comprising an increased olefins content compared to an olefins content of the intermediate dehydrogenation effluent; and, blending the $C_7$ dehydrogenation effluent as a gasoline component in a gasoline pool. An embodiment of the invention is one, any or all of prior embodiments in this paragraph up through the first embodiment in this paragraph further comprising heating the intermediate dehydrogenation effluent before dehydrogenating the intermediate dehydrogenation effluent in the second dehydrogenation zone. An embodiment of the invention is one, any or all of prior embodiments in this paragraph up through the first embodiment in this paragraph wherein the first dehydrogenation zone has a lower inlet temperature than the second dehydrogenation zone. An embodiment of the invention is one, any or all of prior embodiments in this paragraph up through the first embodiment in this paragraph wherein the first dehydrogenation zone is operated with an inlet temperature of between about 400 to 450° C. (752 to 842° F.) and the second dehydrogenation zone is operated with an inlet temperature of about 550° C. (1022° F.). An embodiment of the invention is one, any or all of prior embodiments in this paragraph up through the first embodiment in this paragraph wherein the second dehydrogenation zone is operated to convert between 15-25% to olefins. An embodiment of the invention is one, any or all of prior embodiments in this paragraph up through the first embodiment in this paragraph wherein the $C_7$ dehydrogenation effluent comprises mono-olefins. An embodiment of the invention is one, any or all of prior embodiments in this paragraph up through the first embodiment in this paragraph further comprising isomerizing the stream comprising $C_7$ hydrocarbons, in an isomerization zone comprising a catalyst and operated under conditions to isomerize the $C_7$ hydrocarbons, to provide a $C_7$ isomerized effluent, wherein the $C_7$ isomerized effluent comprises the at least a portion of the stream comprising $C_7$ hydrocarbons dehydrogenated in the first dehydrogenation zone. An embodiment of the invention is one, any or all of prior embodiments in this paragraph up through the first embodiment in this paragraph wherein the catalyst in the first dehydrogenation zone and the catalyst in the second dehydrogenation zone are the same. An embodiment of the invention is one, any or all of prior embodiments in this paragraph up through the first embodiment in this paragraph further comprising isomerizing at least a portion of the stream comprising $C_6$ and lighter boiling hydrocarbons, in a $C_6$ isomerization zone at isomerization conditions, to form a $C_6$ isomerization effluent; reforming the heavy stream, in a reforming zone under reforming conditions, to form a reformate stream; and, blending the $C_6$ isomerization effluent and the reformate stream with the $C_7$ dehydrogenation effluent in the gasoline pool. An embodiment of the invention is one, any or all of prior embodiments in this paragraph up through the first embodiment in this paragraph, further comprising at least one of sensing at least one parameter of the process and generating a signal or data from the sensing; generating and transmitting a signal; or generating and transmitting data.

A second embodiment of the invention is a process for increasing an octane value of a gasoline component, the process comprising separating a naphtha feed in a naphtha splitter into a stream comprising $C_6$ and lighter boiling hydrocarbons, a $C_7$ stream comprising $C_7$ hydrocarbons including methylcyclohexane, and a heavy stream comprising $C_8$ hydrocarbons; isomerizing the stream comprising $C_7$ hydrocarbons in an isomerization zone to provide a $C_7$ isomerized effluent, the isomerization zone comprising a catalyst and operated under conditions to isomerize the $C_7$ hydrocarbons; dehydrogenating the $C_7$ isomerized effluent in a first dehydrogenation zone to form an intermediate dehydrogenation effluent, the first dehydrogenation zone comprising a catalyst and operated under conditions to convert methylcyclohexane to toluene and minimize cracking reactions; dehydrogenating the intermediate dehydrogenation effluent in a second dehydrogenation zone to form a $C_7$ dehydrogenation effluent, the second dehydrogenation zone comprising a catalyst and the $C_7$ dehydrogenation effluent comprising an increased olefins content compared to an olefins content of the intermediate dehydrogenation effluent; and, blending the $C_7$ dehydrogenation effluent as a gasoline component in a gasoline pool. An embodiment of the invention is one, any or all of prior embodiments in this paragraph up through the second embodiment in this paragraph further comprising heating the intermediate dehydrogenation effluent before dehydrogenating the intermediate dehydrogenation effluent in the second dehydrogenation zone. An embodiment of the invention is one, any or all of prior embodiments in this paragraph up through the second embodiment in this paragraph wherein the first dehydrogenation zone has a lower inlet temperature than the second dehydrogenation zone. An embodiment of the invention is one, any or all of prior embodiments in this paragraph up through the second embodiment in this paragraph wherein the first dehydrogenation zone is operated with an inlet temperature of between about 400 to 450° C. (752 to 842° F.) and the second dehydrogenation zone is operated with an inlet temperature of about 550° C. (1022° F.). An embodiment of the invention is one, any or all of prior embodiments in this paragraph up through the second embodiment in this paragraph wherein the second dehydrogenation zone is operated to covert between 15-25% to olefins. An embodiment of the invention is one, any or all of prior embodiments in this paragraph up through the second embodiment in this paragraph wherein the $C_7$ dehydrogenation effluent comprises mono-olefins. An embodiment of the invention is one, any or all of prior embodiments in this paragraph up through the second embodiment in this paragraph wherein the catalyst in the first dehydrogenation zone and the catalyst in the second dehydrogenation zone are the same. An embodiment of the invention is one, any or all of prior embodiments in this paragraph up through the second embodiment in this paragraph, further comprising at least one of sensing at least one parameter of the process and generating a signal or data from the sensing; generating and transmitting a signal; or generating and transmitting data.

A third embodiment of the invention is a process for increasing an octane value of a gasoline component, the process comprising separating a naphtha feed in a naphtha splitter into a stream comprising $C_6$ and lighter boiling hydrocarbons, a $C_7$ stream comprising $C_7$ hydrocarbons including methylcyclohexane, and a heavy stream comprising $C_8$ hydrocarbons; isomerizing at least a portion of the stream comprising $C_6$ and lighter boiling hydrocarbons, in a $C_6$ isomerization zone at isomerization conditions, to form a $C_6$ isomerization effluent; isomerizing the stream comprising $C_7$ hydrocarbons, in an isomerization zone comprising a catalyst and operated under conditions to isomerize the $C_7$ hydrocarbons, to form a $C_7$ isomerized effluent; dehydrogenating the $C_7$ isomerized effluent in a first dehydrogenation zone to form an intermediate dehydrogenation effluent, the first dehydrogenation zone comprising a catalyst and operated under conditions to convert methylcyclohexane to toluene and minimize cracking reactions; heating the intermediate dehydrogenation effluent and then dehydrogenating the intermediate dehydrogenation effluent in a second dehydrogenation zone to form a $C_7$ dehydrogenation effluent, the second dehydrogenation zone comprising a catalyst, the $C_7$ dehydrogenation effluent comprising an increased olefins content compared to an olefins content of the intermediate dehydrogenation effluent; reforming the heavy stream, in a reforming zone under reforming conditions, to form a reformate stream; and, blending the $C_6$ isomerization effluent, the $C_7$ dehydrogenation effluent as the gasoline component, and the reformate stream in a gasoline pool. An embodiment of the invention is one, any or all of prior embodiments in this paragraph up through the third embodiment in this paragraph wherein the first dehydrogenation zone is operated with an inlet temperature of between about 400 to 450° C. (752 to 842° F.) and the second dehydrogenation zone is operated with an inlet temperature of about 550° C. (1022° F.).

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for increasing an octane value of a gasoline component, the process comprising:
separating a naphtha feed in a naphtha splitter into a stream comprising C6 and lighter boiling hydrocarbons, a C7 stream comprising C7 hydrocarbons including C7 paraffins and methylcyclohexane, and a heavy stream comprising C8 hydrocarbons;
dehydrogenating at least a portion of the stream comprising C7 hydrocarbons in a first dehydrogenation zone to form an intermediate dehydrogenation effluent comprising the C7 paraffins and toluene, the first dehydrogenation zone comprising a catalyst and operated under conditions to convert methylcyclohexane to toluene and minimize cracking reactions;
dehydrogenating the intermediate dehydrogenation effluent in a second dehydrogenation zone to form a C7 dehydrogenation effluent, the C7 dehydrogenation zone comprising a catalyst and the C7 dehydrogenation effluent comprising C7 olefins, wherein the C7 dehydrogenation effluent has an increased olefins content compared to an olefins content of the intermediate dehydrogenation effluent; and,
blending the C7 dehydrogenation effluent as a gasoline component in a gasoline pool.

2. The process of claim 1 further comprising:
heating the intermediate dehydrogenation effluent before dehydrogenating the intermediate dehydrogenation effluent in the second dehydrogenation zone.

3. The process of claim 1 wherein the first dehydrogenation zone has a lower inlet temperature than the second dehydrogenation zone.

4. The process of claim 1 wherein the first dehydrogenation zone is operated with an inlet temperature of between about 400 to 450° C. (752 to 842° F.) and the second dehydrogenation zone is operated with an inlet temperature of about 550° C. (1022° F.).

5. The process of claim 1 wherein the second dehydrogenation zone is operated to convert between 15 to 25 wt % of the C7 paraffins to olefins.

6. The process of claim 1 wherein the C7 dehydrogenation effluent comprises mono-olefins.

7. The process of claim 1 further comprising:
isomerizing the stream comprising C7 hydrocarbons, in an isomerization zone comprising a catalyst and operated under conditions to isomerize the C7 hydrocarbons, to provide a C7 isomerized effluent,
wherein the C7 isomerized effluent comprises the at least a portion of the stream comprising C7 hydrocarbons dehydrogenated in the first dehydrogenation zone.

8. The process of claim 1 wherein the catalyst in the first dehydrogenation zone and the catalyst in the second dehydrogenation zone are the same.

9. The process of claim 1 further comprising:
isomerizing at least a portion of the stream comprising C6 and lighter boiling hydrocarbons, in a C6 isomerization zone at isomerization conditions, to form a C6 isomerization effluent;
reforming the heavy stream, in a reforming zone under reforming conditions, to form a reformate stream; and,
blending the C6 isomerization effluent and the reformate stream with the C7 dehydrogenation effluent in the gasoline pool.

10. The process of claim 1 further comprising at least one of:
sensing at least one parameter of the process and generating a signal or data from the sensing;
generating and transmitting a signal; and
generating and transmitting data.

11. A process for increasing an octane value of a gasoline component, the process comprising:
separating a naphtha feed in a naphtha splitter into a stream comprising C6 and lighter boiling hydrocarbons, a C7 stream comprising C7 hydrocarbons including C7 paraffins and methylcyclohexane, and a heavy stream comprising C8 hydrocarbons;
isomerizing the stream comprising C7 hydrocarbons in an isomerization zone to provide a C7 isomerized effluent, the isomerization zone comprising a catalyst and operated under conditions to isomerize the C7 hydrocarbons;
dehydrogenating the C7 isomerized effluent in a first dehydrogenation zone to form an intermediate dehydrogenation effluent comprising the C7 paraffins and toluene, the first dehydrogenation zone comprising a catalyst and operated under conditions to convert methylcyclohexane to toluene and minimize cracking reactions;
dehydrogenating the intermediate dehydrogenation effluent in a second dehydrogenation zone to form a C7 dehydrogenation effluent, the second dehydrogenation zone comprising a catalyst and the C7 dehydrogenation effluent comprising C7 olefins, wherein the C7 dehydrogenation effluent has an increased olefins content compared to an olefins content of the intermediate dehydrogenation effluent; and,
blending the C7 dehydrogenation effluent as a gasoline component in a gasoline pool.

12. The process of claim 11 further comprising:
heating the intermediate dehydrogenation effluent before dehydrogenating the intermediate dehydrogenation effluent in the second dehydrogenation zone.

13. The process of claim 12 wherein the first dehydrogenation zone has a lower inlet temperature than the second dehydrogenation zone.

14. The process of claim 12 wherein the first dehydrogenation zone is operated with an inlet temperature of between about 400 to 450° C. (752 to 842° F.) and the second dehydrogenation zone is operated with an inlet temperature of about 550° C. (1022° F.).

15. The process of claim 12 wherein the second dehydrogenation zone is operated to covert between 15 to 25 wt % of the C7 paraffins to olefins.

16. The process of claim 12 wherein the C7 dehydrogenation effluent comprises mono-olefins.

17. The process of claim 12 wherein the catalyst in the first dehydrogenation zone and the catalyst in the second dehydrogenation zone are the same.

18. The process of claim 12 further comprising at least one of:

sensing at least one parameter of the process and generating a signal or data from the sensing;
generating and transmitting a signal; and
generating and transmitting data.

19. A process for increasing an octane value of a gasoline component, the process comprising:
separating a naphtha feed in a naphtha splitter into a stream comprising C6 and lighter boiling hydrocarbons, a C7 stream comprising C7 hydrocarbons including C7 paraffins and methylcyclohexane, and a heavy stream comprising C8 hydrocarbons;
isomerizing at least a portion of the stream comprising C6 and lighter boiling hydrocarbons, in a C6 isomerization zone at isomerization conditions, to form a C6 isomerization effluent;
isomerizing the stream comprising C7 hydrocarbons, in an isomerization zone comprising a catalyst and operated under conditions to isomerize the C7 hydrocarbons, to form a C7 isomerized effluent comprising isomerized C7 paraffins;
dehydrogenating the C7 isomerized effluent in a first dehydrogenation zone to form an intermediate dehydrogenation effluent comprising the isomerized C7 paraffins and toluene, the first dehydrogenation zone comprising a catalyst and operated under conditions to convert methylcyclohexane to toluene and minimize cracking reactions;
heating the intermediate dehydrogenation effluent and then dehydrogenating the intermediate dehydrogenation effluent in a second dehydrogenation zone to form a C7 dehydrogenation effluent, the second dehydrogenation zone comprising a catalyst, the C7 dehydrogenation effluent comprising C7 olefins, wherein the C7 dehydrogenation effluent has an increased olefins content compared to an olefins content of the intermediate dehydrogenation effluent;
reforming the heavy stream, in a reforming zone under reforming conditions, to form a reformate stream; and,
blending the C6 isomerization effluent, the C7 dehydrogenation effluent as the gasoline component, and the reformate stream in a gasoline pool.

20. The process of claim 19 wherein the first dehydrogenation zone is operated with an inlet temperature of between about 400 to 450° C. (752 to 842° F.) and the second dehydrogenation zone is operated with an inlet temperature of about 550° C. (1022° F.).

* * * * *